US012558485B2

(12) United States Patent
Jeon et al.

(10) Patent No.: US 12,558,485 B2
(45) Date of Patent: Feb. 24, 2026

(54) NEEDLELESS SYRINGE HAVING MULTI-NOZZLE AND MANUFACTURING METHOD THEREFOR

(71) Applicant: JSKBIOMED INC., Daegu (KR)

(72) Inventors: Jin Woo Jeon, Incheon (KR); Joon Hak Park, Cheonan-si (KR); Min Sung Kim, Naju-si (KR); Kwang Il Choi, Daejeon (KR)

(73) Assignee: JSKBIOMED INC., Daejeon (KR)

( * ) Notice: Subject to any disclaimer, the term of this patent is extended or adjusted under 35 U.S.C. 154(b) by 1040 days.

(21) Appl. No.: 17/637,413

(22) PCT Filed: Aug. 21, 2020

(86) PCT No.: PCT/KR2020/011153
§ 371 (c)(1),
(2) Date: Feb. 22, 2022

(87) PCT Pub. No.: WO2021/040324
PCT Pub. Date: Mar. 4, 2021

(65) Prior Publication Data
US 2022/0273880 A1      Sep. 1, 2022

(30) Foreign Application Priority Data
Aug. 26, 2019     (KR) ........................ 10-2019-0104631

(51) Int. Cl.
A61M 5/30          (2006.01)
(52) U.S. Cl.
CPC ... A61M 5/3007 (2013.01); *A61M 2205/0211* (2013.01); *A61M 2207/00* (2013.01)
(58) Field of Classification Search
CPC ...... A61M 5/2046; A61M 5/286; A61M 5/30; A61M 5/3007; A61M 5/19;
(Continued)

(56) References Cited

U.S. PATENT DOCUMENTS 6,981,961 B1    1/2006  Navelier et al.
7,559,917 B2 *  7/2009  Alexandre .............. A61M 5/30
                                                          604/143
(Continued)

FOREIGN PATENT DOCUMENTS

CN        1361703 A       7/2002
CN      104470578 A       3/2015
(Continued)

OTHER PUBLICATIONS

European Search Report of European U.S. Appl. No. 20/857,007 mailed Jul. 26, 2023.
(Continued)

*Primary Examiner* — Chelsea E Stinson
*Assistant Examiner* — Alexandra LaLonde
(74) *Attorney, Agent, or Firm* — Revolution IP, PLLC

(57)          ABSTRACT

The present disclosure relates to a needleless syringe having a multi-nozzle which includes an upper housing defining a chamber for containing a pressure-generating liquid and including a pressure-generating unit at an upper portion of the upper housing, a lower housing configured to contain a drug solution and coupled to a lower portion of the upper housing, an elastic membrane disposed between the upper housing and the lower housing to separate the pressure-generating liquid from the drug solution, an outer chamber attached to a lower portion of the lower housing and having an insertion portion in fluid communication with an interior of the lower housing, an inner chamber inserted into the insertion portion, the inner chamber having a plurality of branch grooves on an outer surface of the inner chamber, and a plurality of injection nozzles coupled to a lower portion of the inner chamber.

7 Claims, 8 Drawing Sheets

(58) Field of Classification Search
CPC ...... A61M 5/31511; A61M 2205/0211; A61M
2207/00; A61M 2005/3022
See application file for complete search history.

(56) References Cited

U.S. PATENT DOCUMENTS

| | | | |
|---|---|---|---|
| 10,507,287 B2 | 12/2019 | Jeon | |
| 2007/0055214 A1* | 3/2007 | Gilbert | A61M 5/30 |
| | | | 604/500 |
| 2011/0230826 A1 | 9/2011 | Yoh et al. | |
| 2013/0066263 A1 | 3/2013 | Yoh et al. | |

FOREIGN PATENT DOCUMENTS

| | | | |
|---|---|---|---|
| CN | 108066852 | A | 5/2018 |
| EP | 2875843 | A1 | 5/2015 |
| JP | 2004-329635 | A | 11/2004 |
| JP | 2004-358234 | A | 12/2004 |
| KR | 10-2012-0105718 | A | 9/2012 |
| KR | 10-1192764 | B1 | 10/2012 |
| KR | 10-2018-0040994 | A | 4/2018 |
| KR | 10-2019-0049097 | A | 5/2019 |
| TW | 201109054 | A | 3/2011 |
| WO | 2004-093818 | A2 | 11/2004 |

OTHER PUBLICATIONS

International Search Report for PCT/KR2020/011153 mailed Apr. 5, 2021 from Korean Intellectual Property Office.

* cited by examiner

400

NEEDLELESS SYRINGE HAVING MULTI-NOZZLE AND MANUFACTURING METHOD THEREFOR

CROSS REFERENCE TO PRIOR APPLICATIONS

This application is a National Stage Application of PCT International Patent Application No. PCT/KR2020/011153 filed on Aug. 21, 2020, under 35 U.S.C. § 371, which claims priority to Korean Patent Application No. 10-2019-0104631 filed on Aug. 26, 2019, which are all hereby incorporated by reference in their entirety.

TECHNICAL FIELD

The present disclosure relates to a needleless syringe having a multi-nozzle. More particularly, the present disclosure relates to a needleless syringe having a multi-nozzle and a manufacturing method therefor, wherein the needleless syringe is configured to spray a drug solution through an injection nozzle as energy generated in a pressure-generating unit inflates a pressure-generating liquid, and has a precise branch channel that is stably formed so as to spray the drug to a plurality of parts by using a plurality of injection nozzles.

BACKGROUND ART

A drug delivery system refers to a dosage form designed to efficiently deliver a necessary amount of a drug to the body while minimizing the side effects that occur in an existing method and maximizing the therapeutic effect of the drug in using a drug for the treatment of diseases or wounds in the human body. Among numerous types of drug delivery methods that have been released so far, an injection method using a needle is the most used due to stability and efficiency thereof.

Meanwhile, the drug delivery system using a needle can perform precise and efficient drug delivery, but has problems such as patient phobia of injection due to pain during injection, a risk of causing infection due to reuse, and generation of a large amount of medical waste.

In order to overcome the above problems, various types of new methods such as powder injection, liquid jet injection, and a microneedle have been developed as a new drug delivery system, but there are still problems to be solved.

Among the methods of the drug delivery system as described above, the liquid jet method using a piezoelectric actuator is configured to inject a drug solution at a high speed to penetrate the skin tissue and inject the drug solution. The above-described method, which was first developed in the 1930's, has been used to deliver many types of macromolecules, drugs such as insulin and growth hormone, and vaccines into the human body. However, the liquid jet method has not been popularized due to problems such as rebounding that occurs during jet injection, instability of delivered drug dose and penetration depth, and considerable pain of injection.

Instead of the method using a piezoelectric actuator as described above, a microjet injector using pressure generation induction by high energy has also been recently developed. Among drug delivery systems that have been recently studied, a biolistic method in which micro-particles are directly accelerated and a drug jet delivery method in which a drug solution penetrates in the form of a jet show potential to solve the greatest weakness of the existing systems such as patient phobia of injection, causing pain, and causing wounds, so there is great anticipation for the methods.

In addition, a microjet injector using high energy, for example, using laser as a high energy source, by induction of pressure generation is a pulse laser beam used as a power source of a liquid jet of microscopically spraying a drug, a chamber containing a solution and a drug, and an elastic membrane separating the drug from the solution, and a nozzle with a diameter of 300 μm or less through which the liquid jet is injected In the above-described microjet injector, when the pulsed laser beam is focused on the pressure chamber in which the liquid is stored, an explosive phase change occurs due to instantaneous high energy transfer to a local area, and the surrounding materials are instantaneously evaporated to form bubbles. As the pressure in the pressure chamber increases (volume expansion due to shock waves and bubbles), the elastic membrane is expanded toward the drug, and the expansion of the elastic membrane pushes the drug out of the nozzle. As a high pressure is generated at an outlet of the nozzle, the drug that has passed through the nozzle with a diameter of 300 μm or less is injected at a high speed as a liquid jet with a diameter of 300 μm or less.

However, the conventional microjet injector includes only one drug injection nozzle, so one drug delivery is performed at one instantaneous high-energy delivery. Therefore, when a drug delivery with the conventional microjet injector performing to a plurality of parts is required such as dermatological treatments, there is a problem that the treatment takes a long time.

In order to above problem, the conventional microjet injector has been configured to have a plurality of nozzles, but when the number of injection nozzles is increased, the pressure to be injected is reduced, and there is a limit in increasing the number of injection nozzles.

Furthermore, when the number of the injection nozzles of the conventional microjet injector is increased, the number of flow channels through which a drug branches is increased, so there is a problem in that it is difficult to precisely form the flow paths.

DISCLOSURE

Technical Problem

Accordingly, the present disclosure has been made keeping in mind the above problems occurring in the related art, and the present disclosure is intended to provide a needleless syringe having a multi-nozzle and a manufacturing method therefor, wherein the needless syringe is configured to deliver pressure to a nozzle part by using energy transmitted from one energy-generating part and has a precise branch channel in order to deliver a drug to a plurality of parts by only one pressure source.

Another objective of the present disclosure is intended to provide a needleless syringe having a multi-nozzle and a manufacturing method therefor, wherein stable and precise branch channels are formed such that an inner chamber that is inserted into an outer chamber to form a plurality of branch channels is coupled to or insert-injection molded to the outer chamber or a plurality of inner chambers, which are inserted into the outer chamber and coupled to each other to face each other to form a plurality of branch channels, is coupled to or insert-injection molded to the outer chamber.

Technical Solution

In order to accomplish the above object, the present disclosure provides a needleless syringe having a multi-nozzle, the needleless syringe including an upper housing configured to be filled with a pressure-generating liquid therein and including a pressure-generating unit at an upper portion thereof, a lower housing configured to be filled with a drug solution therein and coupled to a lower portion of the upper housing, an elastic membrane provided between the upper housing and the lower housing and configured to separate the pressure-generating liquid and the drug solution from each other, an outer chamber coupled to a lower portion of the lower housing and having an insertion portion communicating with an inside space of the lower housing, an inner chamber inserted into the insertion portion and providing a plurality of branch channels, and a plurality of injection nozzles coupled to a lower portion of the inner chamber and having injection channels connected to the branch channels.

The injection nozzles may be made of a zirconium-based ceramic material. The lower housing may include an injector provided outside the lower housing and communicating with the inside space of the lower housing.

The insertion portion may be shaped to be gradually expanded in a downward direction, the inner chamber may have a plurality of branch grooves formed from a center portion of an upper end thereof in the downward direction, and the branch channels may be provided such that the inner chamber may be inserted into the insertion portion and then outer sides of the branch grooves may be sealed by an inner surface of the insertion portion.

The inner chamber may include a first chamber inserted into a first portion of the insertion portion, and a plurality of first branch grooves on an inner surface thereof, the first branch grooves being formed from a center portion of an upper end of the inner chamber in a downward direction, and a second chamber inserted into a second portion of the insertion portion to face the first chamber, wherein the branch channels may be provided such that outer sides of the first branch grooves may be sealed by an inner surface of the second chamber.

The inner chamber may include a first chamber inserted into a first portion of the insertion portion, and a plurality of first branch grooves on an inner surface thereof, the first branch grooves being formed from a center portion of an upper end of the inner chamber in a downward direction, and a second chamber inserted into a second portion of the insertion portion to face the first chamber, and having a plurality of second branch grooves formed on an inner surface thereof to face the plurality of first branch grooves, wherein the branch channels may be provided such that the first branch grooves and the second branch grooves may communicate with each other.

Advantageous Effects

According to the needleless syringe having a multi-nozzle and the manufacturing method therefor of the present disclosure as described above, an interval between the nozzles can be densely arranged using the one energy-generating part. Therefore, when several injection into an affected part is required, usage of a plurality of injection nozzles can reduce the treatment time.

Furthermore, according to the present disclosure, the inner chamber is inserted into and coupled to or insert-injection molded to the outer chamber, so that the stable and precise branch channels can be formed. Therefore, a plurality of drugs can be stably injected into an affected area by the plurality of injection nozzles.

DETAILED DESCRIPTION FOR REFERENCE NUMERALS

Figure 1:
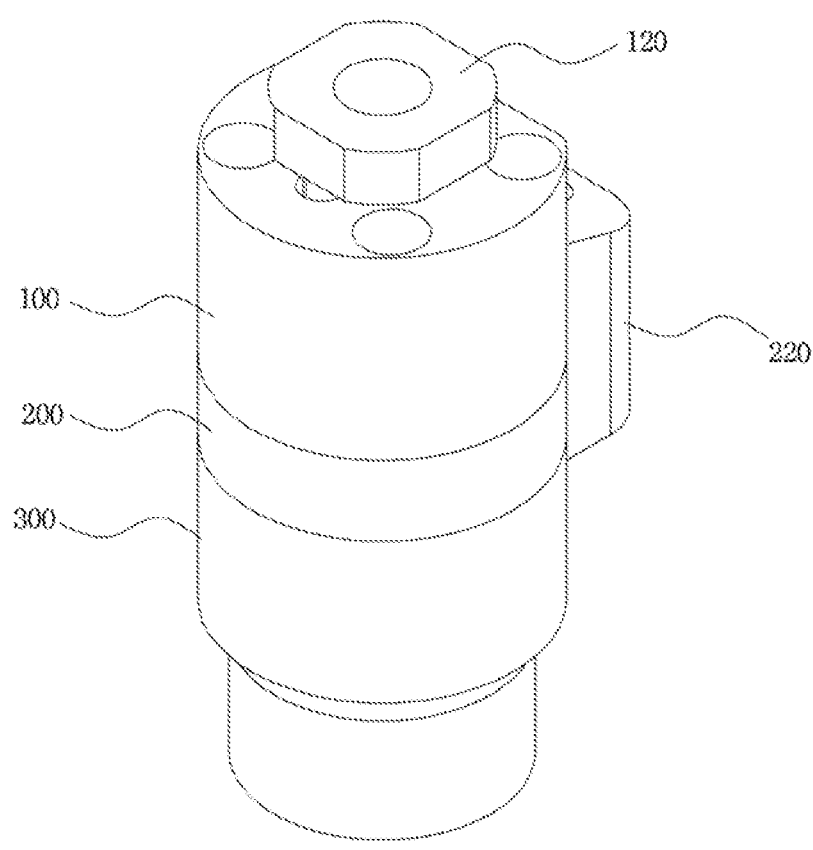
FIG. 1 is a perspective view showing a 4-hole type syringe according to an exemplary embodiment of the present disclosure.
Figure 2:
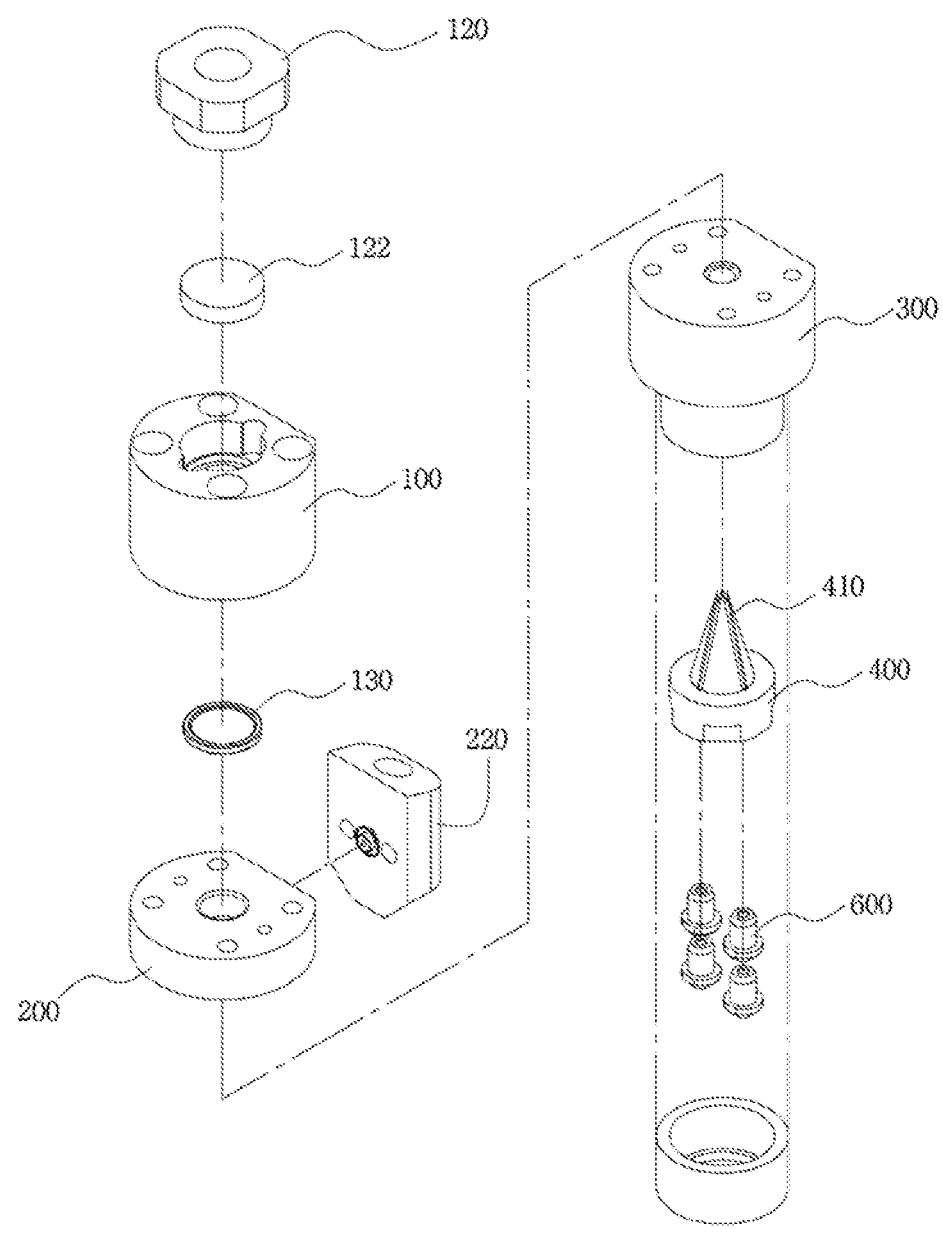
FIG. 2 is an exploded-perspective view showing the 4-hole type syringe according to the exemplary embodiment of the present disclosure.
Figure 3:
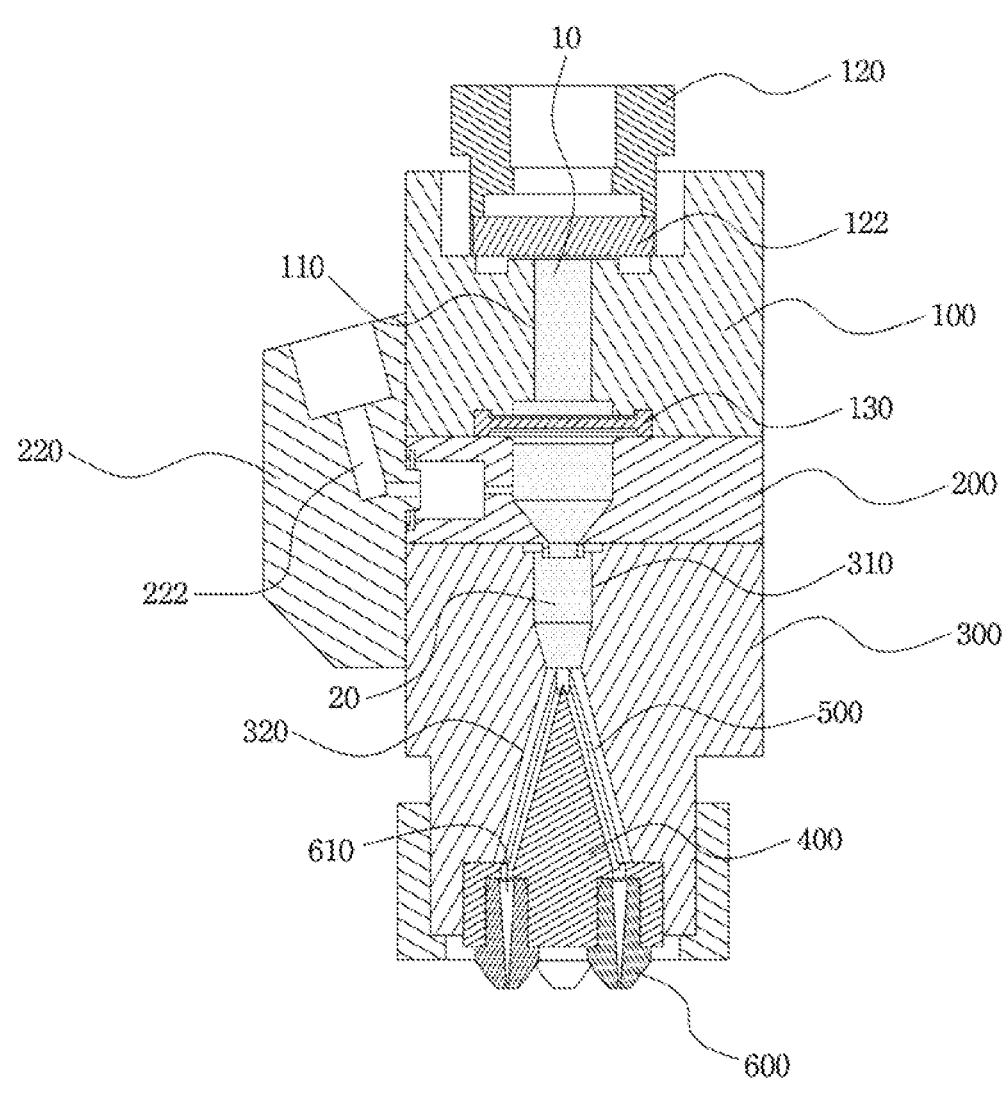
FIG. 3 is a lateral sectional view showing the 4-hole type syringe according to the exemplary embodiment of the present disclosure.
Figure 4:
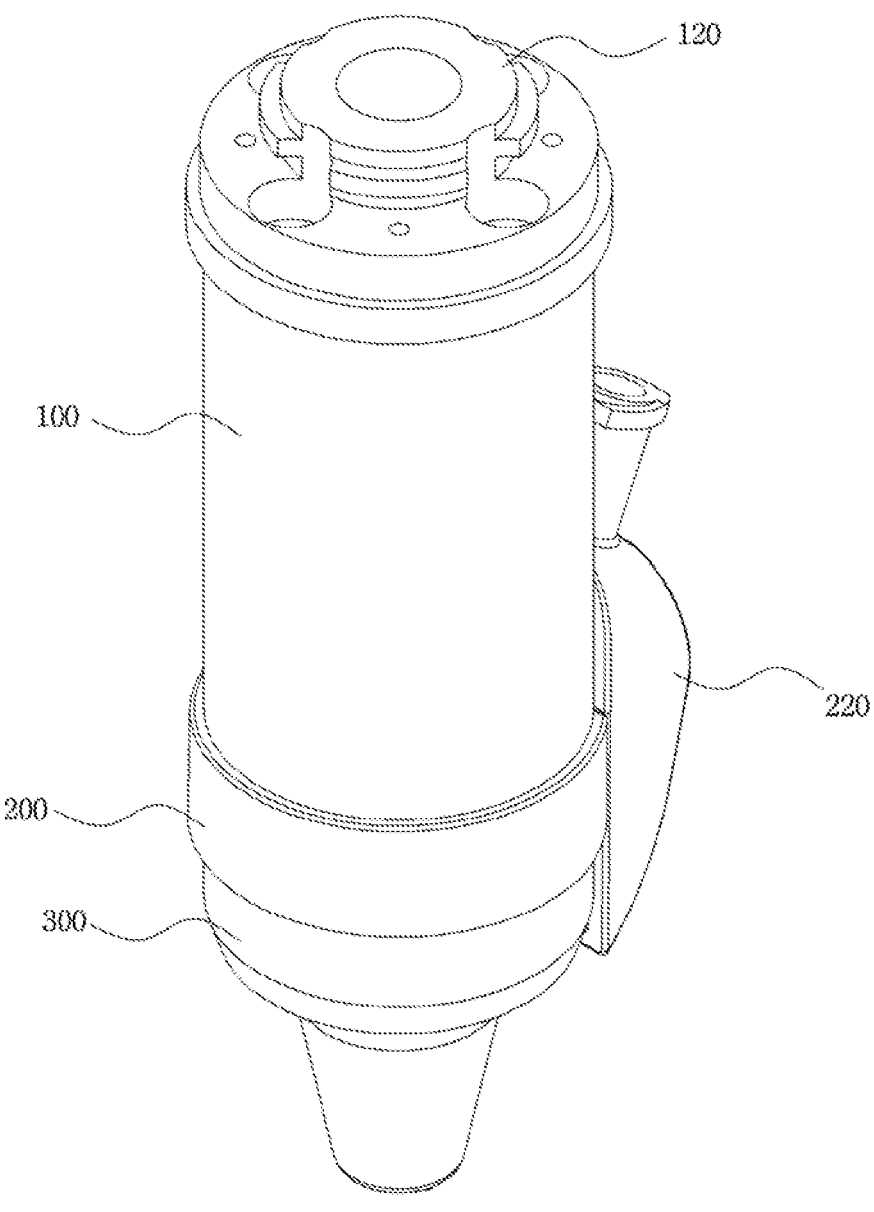
FIG. 4 is a perspective view showing a two-hole type syringe according to another embodiment of the present disclosure.
Figure 5:
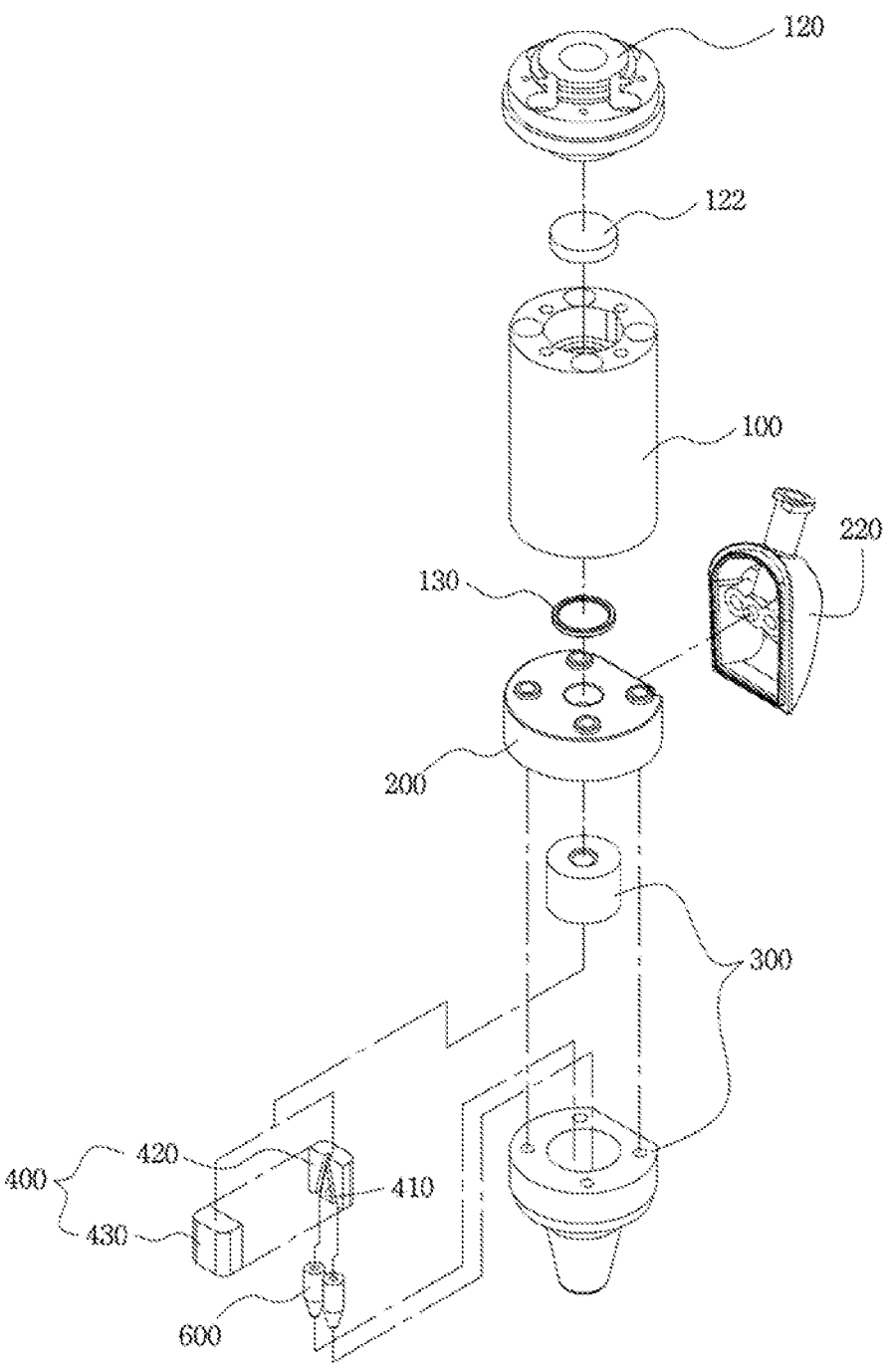
FIG. 5 is an exploded-perspective view showing the two-hole type syringe according to the another embodiment of the present disclosure.
Figure 6:
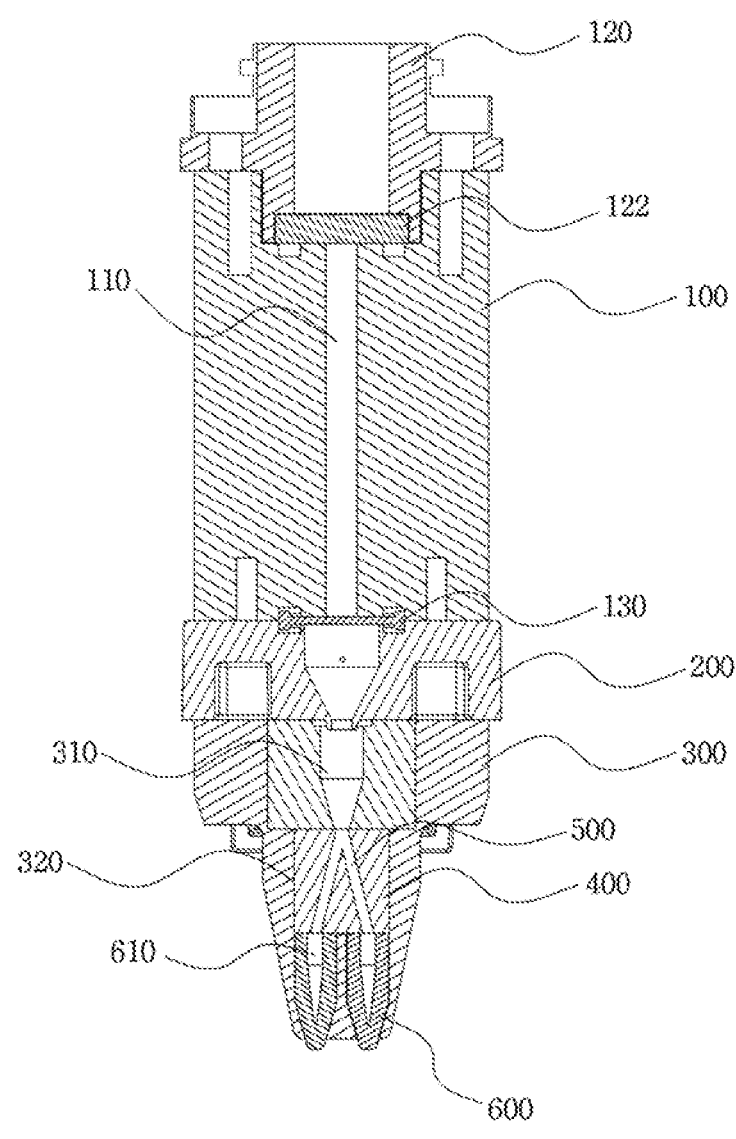
FIG. 6 is a front sectional view showing the two-hole type syringe according to the present disclosure.
Figure 7:
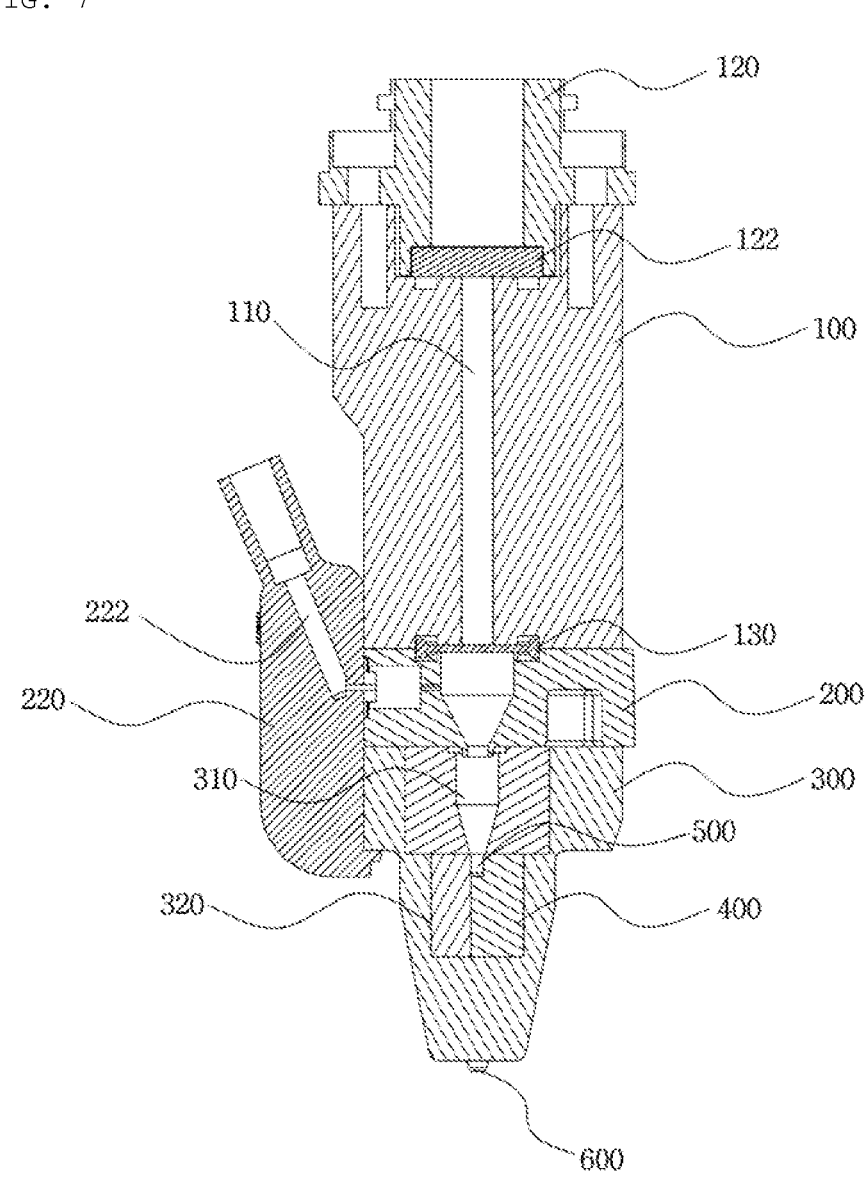
FIG. 7 is a lateral sectional view showing the two-hole type syringe according to the another embodiment of the present disclosure.
Figure 8:
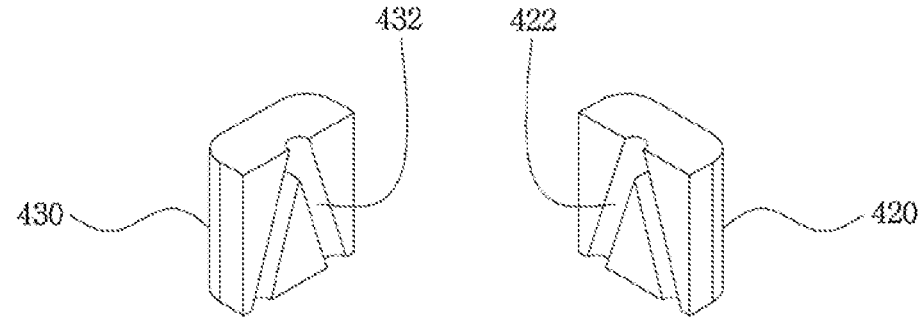
FIG. 8 is a perspective view showing first and second chambers of the two-hole type syringe another embodiment of the present disclosure.

10: pressure-generating liquid
20: drug solution
100: upper housing 110: upper space portion
120: pressure-generating unit 130: elastic membrane
200: lower housing 210: lower space portion
220: injector 300: outer chamber
310: branch portion 320: insertion portion
400: inner chamber 410: branch groove
420: first chamber 422: first branch groove
430: second chamber 432: second branch groove
500: branch channel 600: injection nozzle
610: injection channel

MODE FOR INVENTION

The present disclosure relates to a needleless syringe having a multi-nozzle (hereinbelow, which refers to as 'the syringe') and, more particularly, to a needleless syringe having a multi-nozzle and a manufacturing method therefor. In order to deliver a drug to a plurality of parts with one energy generating part and one syringe, the syringe of the present disclosure includes a plurality of injection nozzles 600 so that when several injections into an affected part are needed, the one syringe may stably and precisely deliver the drug to the plurality of parts. In addition, in order to stably move the drug into the plurality of injection nozzles 600, an inner chamber 400 is inserted into and then is coupled to or insert-injection molded to an outer chamber 300, so that branch channels 500 may be precisely formed. Therefore, injection channels 610 of the injection nozzles 600 made of a zirconium-based ceramic material and the branch channels 500 may stably and precisely communicate with each other, so that molding performance is improved and thus the production of defective products in manufacturing may be minimized.

For achieving the present disclosure as described above, the syringe includes: an upper housing 100 filled with a pressure-generating liquid 10 therein and including a pressure-generating unit 120 at an upper portion thereof; a lower housing 200 filled with a drug solution 20 therein and coupled to a lower portion of the upper housing 100; an elastic membrane 130 provided between the upper housing 100 and the lower housing 200 and separating the pressure-generating liquid 10 and the drug solution 20 from each other; the outer chamber 300 coupled to a lower portion of the lower housing 200 and having an insertion portion 320 communicating with the inside space of the lower housing 200; the inner chamber 400 inserted into the insertion portion 320 and forming the plurality of branch channels 500; and the plurality of injection nozzles 600 coupled to a lower portion of the inner chamber 400, and having the injection channels 610 coupled to the branch channels 500.

Furthermore, the injection nozzles 600 of the present disclosure are made of a zirconium-based ceramic material. The lower housing 200 includes an injector 220 provided outside the lower housing 200 and communicating with the inside portion of the lower housing 200.

Furthermore, the insertion portion 320 of the present disclosure has the shape that is gradually expanded in a downward direction. The inner chamber 400 includes branch grooves 410 formed from a center portion of an upper end of the inner chamber 400 in the downward direction. The branch channels 500 are formed such that the inner chamber 400 is inserted into the insertion portion 320 and then an inner surface of the insertion portion 320 seals outer sides of the branch grooves 410.

Furthermore, the inner chamber 400 of the present disclosure includes: a first chamber 420 inserted into a first portion of the insertion portion 320 and having a plurality of first branch grooves 422 on an inner surface thereof, the first branch grooves 422 being formed from the center portion of the upper end in the downward direction; and a second chamber 430 inserted into a second portion of the insertion portion 320 to face the first chamber 420. The branch channels 500 are formed such that an inner surface of the second chamber 430 seals outer sides of the first branch grooves 422.

Furthermore, the inner chamber 400 of the present disclosure includes: the first chamber 420 inserted into the first portion of the insertion portion 320, and having the first branch grooves 422 on the inner surface, the first branch grooves 422 being formed from the center portion of the upper end of the first chamber 420 in the downward direction; and the second chamber 430 inserted into the second portion of the insertion portion 320 to face the first chamber 420 and having the plurality of second branch grooves 432 formed on an inner surface of the second chamber 430 to face the plurality of first branch grooves 422. The branch channels 500 are formed such that the first branch grooves 422 and the second branch grooves 432 communicated with each other.

Hereinbelow, the present disclosure will be described in detail with reference to FIGS. 1 to 9 showing embodiments of the present disclosure.

First, the syringe of the present disclosure may adopt various materials, such as stellite, aluminum alloy, zirconium-based ceramic, etc., that do not interfere with achieving the function of the present disclosure. Specifically, in order to precise inject the drug solution 20, the injection nozzles 600 is preferably made of a zirconium-based ceramic material.

In addition, the syringe of the present disclosure has the branch channels 500 are connected to and communicate with the precise injection channels 610 formed in the injection nozzles 600 made of a zirconium-based ceramic material. Therefore, the drug solution 20 may be more stably delivered through the injection nozzles 600 and easy manufacturing of the syringe is possible, whereby an effect of reducing manufacturing cost and time is realized.

As a main component for achieving the present disclosure, the upper housing 100 is filled with the pressure-generating liquid 10 therein and including the pressure-generating unit 120 at the upper portion thereof. An upper space portion 110 is provided in the upper housing 100 and the pressure-generating liquid 10 is filled into the upper space portion 110. Energy generated by the pressure-generating unit 120 is transmitted to the inside space of the upper space portion 110, i.e. the pressure-generating liquid 10, and an increased pressure of the upper space portion 110 is transmitted to a lower space portion 210 by the elastic membrane 130, which will be described in detail later.

Specifically, the upper housing 100 of the present disclosure is formed to have the length in a vertical direction. A hollow with open upper and lower portions, i.e. the upper space portion 110 is formed in a longitudinal direction. The lower portion of the upper space portion 110 is sealed by the elastic membrane 130, which will be described in detail later. Meanwhile, the pressure-generating unit 120 is provided at the upper portion of the upper housing 100 to seal the upper portion of the upper space portion 110 after the upper space portion 110 is filled with the pressure-generating liquid 10 therein, and to focus and apply the energy to the pressure-generating liquid 10 filled in the upper space portion 110.

Herein, the pressure-generating liquid 10 is composed of a liquid mixed with a reflector or an opaque material or an opaque liquid. The above configuration is to prevent the drug solution 20 from being altered as when the energy, i.e. laser, is focused to a portion filled with the pressure-generating liquid 10, i.e. the upper space portion 110, as high energy such as laser passes through the elastic membrane 130 and then reaches the drug solution 20.

Specifically, normal water may be used as the pressure-generating liquid 10 and high polymer sols and gels such as alcohol or polyethylene glycol, etc. may be used, and a degassed liquid may be preferably used to minimize residual bubbles in generation of bubbles.

Furthermore, as the pressure-generating liquid 10, when an electrolyte (salt, etc.) is added into pure water, molecules are ionized and thus energy required to collapse molecular structures of the liquid is reduced, so that it is preferable that the bubbles may be generated with better efficiency.

In addition, the pressure-generating unit 120 seals the upper portion of the upper space portion 110 and focuses and applies the energy to the pressure-generating liquid 10 filled in the upper space portion 110. Therefore, when the volume of the pressure-generating liquid 10 is expanded, the elastic membrane 130, which will be described in detail later, is stretched and thus an instantaneous pressure is applied to the drug solution 20 filled in the lower space portion 210, which will be described in detail later, so that an effect capable of microjet-injecting the drug solution 20 through the injection nozzles is implemented.

Specifically, the pressure-generating unit 120 may preferably adopt a laser-generating device, which generates and emits a laser beam so that the laser beam is focused to the pressure-generating liquid 10 filled in the upper space portion 110, or an electrode through which electric energy passes through.

Herein, as an embodiment, the pressure-generating unit 120 used in the syringe of the present disclosure is composed of a laser-generating device, and a transparent lens 122 transmitting laser generated in the laser-generating device to the upper space portion 110. The transparent lens 122 seals the upper portion of the upper space portion 110 and the laser-generating device is provided on an upper portion of the transparent lens 122.

In addition, the laser-generating device may adopt various devices that may generate laser to expand the pressure-generating liquid 10 filled in the upper space portion 110 of the upper housing 100 through the transparent lens 122, and generate energy by using microwaves, laser, etc.

In other words, the laser-generating device focuses the generated laser, through the transparent lens 122, to the pressure-generating liquid 10 filled in the upper space portion 110. The instantaneous expansion due to evaporation of the pressure-generating liquid 10 (increasing inner pressure of the upper space portion 110) and transmission of shock waves allows the drug solution 20 filled in the lower space portion 210 of the lower housing 200, which will be described in detail later, to be rapidly pushed to the injection channels 610 to generate a microjet.

In addition, in the embodiment, the transparent lens 122 is shown as an example in which the transparent lens 122 blocks a part of an upper portion of the upper space portion 110, i.e., a part of an upper surface of the upper housing 100, but the present disclosure is not limited thereto. The transparent lens 122 may be obviously provided to block the entire upper surface of the upper housing 100, and may have various shapes that can perform light transmission such as convex and concave.

In addition, the elastic membrane 130 of the present disclosure seals the lower portion of the upper space portion 110. The elastic membrane 130 is provided between the upper housing 100 and the lower housing 200, which will be described later in detail, and partitions the upper space portion 110 from the lower space portion 210 of the lower housing 200 to separate the pressure-generating liquid 10 and the drug solution 20 from each other. The elastic membrane 130 transmits a pressure, which is increased in the upper space portion 110 filled with the pressure-generating liquid 10, to the lower space portion 210 filled with the drug solution 20.

Herein, the elastic membrane 130 may be a membrane having elasticity such as silicone rubber. The present disclosure is not limited to the above configuration, but the elastic membrane 130 may be variously embodied such as a plate-shaped disc vertically reciprocated, thereby transmitting that the pressure applied into the space filled with the pressure-generating liquid 10 to the lower space portion 210 filled with the drug solution 20.

As a main component for achieving the present disclosure, the lower housing 200 is filled with the drug solution 20 and is coupled to the lower portion of the upper housing 100. The lower housing 200 has the lower space portion 210 therein, and the lower space portion is filled with the drug solution 20. The lower housing 200 is coupled to the lower portion of the upper housing 100 so that the upper space portion 110 and the lower space portion 210 communicate with each other. When the pressure-generating liquid 10 inflates and the pressure in the upper space portion 110 is increased by the energy generated from the energy-generating part, the elastic membrane 130 transmits the increased pressure to the lower space portion 210 and thus the drug solution 20 filled in the lower housing 200 moves downward. Therefore, the drug solution 20 is injected through the injection nozzles 600, which will be described in detail later.

Specifically, the lower housing 200 of the present disclosure is formed with the length in the vertical direction same as the upper housing 100. A hollow with open upper and lower portions, i.e. the lower space portion 210, is formed in the longitudinal direction of the lower housing. The lower space portion 210 communicates with the upper space portion 110 of the upper housing 100 and is partitioned by the elastic membrane 130. Meanwhile, while the drug solution 20 filled in the lower space portion 210 remains in a filled state without leakage by the outer chamber 300, the inner chamber 400, and the injection nozzles 600, which will be described in detail later, the increased pressure of the upper space portion 110 is transmitted by the laser generated by the energy-generating part, i.e. the pressure-generating unit 120 thereby allowing the drug solution 20 to be injected through the injection nozzles 600.

In addition, the lower housing 200 of the present disclosure includes the injector 220 provided outside the lower housing 200 and having an injection flow path 222 communicating with the lower space portion 210. The injector 220 realizes an effect of filling the drug solution 20 into the lower space portion 210 by the drug solution 20 that has been injected.

In addition, the lower housing 200 of the present disclosure has an injection portion (not shown) communicating with a lateral surface of the lower space portion 210. The injector 220 is provided such that the injection portion communicates with the injection flow path 222, and the injector 220 includes a drug supply portion (not shown) communicating with the injection flow path 222. Therefore, when the drug solution 20 filled in the lower space portion 210 is injected, the injector 220 may allow the drug solution 20 to be filled by an injected amount of the drug solution 20 into the lower space portion 210 from the drug supply portion through the injection flow path 222 and the injection portion and maintain the drug solution 20 in the state in which the drug solution may be delivered.

As a main component achieving the present disclosure, the outer chamber 300 includes the insertion portion 320 coupled to the lower portion of the lower housing 200, and communicating with the inside space of the lower housing 200. The outer chamber 300 is configured such that the inner chamber 400 is inserted into and coupled to or insert-injection molded to the insertion portion 320. Therefore, the drug solution 20 filled in the above-described lower space portion 210 of the lower housing 200 is moved and then branches through the plurality of branch channels 500 formed by the inner chamber 40, so that the drug solution 20 is finally delivered to a plurality of parts through the injection nozzles 600, which will be described in detail later.

In addition, the outer chamber 300 of the present disclosure is provided such that a branch portion 310 communicating with the lower space portion 210 of the lower housing 200 is provided on an upper portion of the insertion portion 320. The branch portion 310 is filled with the drug solution 20 while communicating with the above-described lower space portion 210 of the lower housing 200. The branch portion 310 may efficiently move the drug solution 20 through the branch channels 500, which will be described in detail later.

In addition, the insertion portion 320 has the branch channels 500 so as to separate the drug solution 20 filled in the branch portion 310 into a plurality of directions. The insertion portion 320 has the branch channels 500 as the inner chamber 400, which will be described in detail later, is provided therein.

As a main component for achieving the present disclosure, the inner chamber 400 is inserted into the insertion portion 320 and forms the plurality of branch channels 500. The inner chamber 400 is inserted into and is coupled to or insert-injection molded to the insertion portion 320 of the outer chamber 300 to form the plurality of branch channels 500. Therefore, the drug solution 20 moved from the branch portion 310 branches while passing through the branch channels 500 and then is moved to the injection nozzles 600, which will be described in detail later.

Specifically, according to an embodiment of the present disclosure, the inner chamber 400 allows an inner surface of the above-described insertion portion 320 of the outer chamber 300 to partially form outer surfaces of the branch channels 500 and a plurality of flow path grooves is provided to form remaining portions of the outer surfaces of the branch channels 500, thereby forming the branch channels 500.

In addition, according to the embodiment, the insertion portion 320 of the outer chamber 300 is formed to communicate with the branch portion 310 while having the shape that is gradually expanded in the downward direction. In other words, the insertion portion 320 is shaped in a conical shape. As the inner chamber 400, which will be described in detail later, is inserted into and coupled to the insertion portion 320, the insertion portion 320 may form the branch channels 500 with precise and stable formation of the branch channels 500, whereby the drug solution 20 may efficiently branch and be moved.

In addition, the injection nozzles 600, which will be described in detail later, used in the syringe of the present disclosure is made of zirconium oxide (zirconia) of a zirconium-based ceramic material. Zirconium oxide has low thermal conductivity so as to prevent the drug solution 20 from being altered due to thermal transfer when high energy i.e. laser is emitted, and has high fracture toughness and high resistance to fracture propagation so as to prevent an end of a spray channel from being broken or deformed in microjet injection. However, due to the nature of the material of the zirconium oxide, precise molding of the injection channels 610 is difficult and a manufacturing cost is increased in order to perform the precise molding.

Therefore, the branch channels 500 are precisely formed to communicate with the injection channels 610 of the injection nozzles 600 so that the drug solution 20 is stably moved. However, the syringe of the present disclosure is configured such that the inner chamber 400 is inserted into and coupled to or insert-injection molded to the inside space of the outer chamber 300, so that the branch channels 500 may be precisely formed and assembly, i.e. manufacturing of the syringe may be easy. Therefore, there may be an effect of reducing the manufacturing cost and time of the syringe.

In other words, in the syringe of the present disclosure, the branch channels 500 may be stably and precisely formed by the method in which the outer chamber 300 is coupled to the lower portion of the above-described lower housing 200 and the inner chamber 400 is inserted into and coupled to or insert-injection molded to the insertion portion 320 provided in the outer chamber 300.

In detail, the inner chamber 400 of the present disclosure is formed in the shape corresponding to the insertion portion 320 having the conical shape according to the embodiment of the outer chamber 300 and is inserted into the insertion portion 320. The inner chamber 400 includes the plurality of branch grooves 410 formed from the center portion of the upper end of the inner chamber 400 in the downward direction. The branch channels 500 are formed such that the inner chamber 400 is inserted into the insertion portion 320 of the outer chamber 300 and then an inner surface of the insertion portion 320 seals outer sides of the branch grooves 410.

In other words, the outer chamber 300 and the inner chamber 400 of the present disclosure stably form the branch channels 500, which is difficultly molded at once, in the insert method, and allow the drug solution 20 to be moved into the precisely formed branch channels 500. As a result, the outer chamber 300 and the inner chamber 400 realize an effect of delivering, i.e. injecting the drug solution 20 through the injection nozzles 600, which will be described in detail later.

In addition, in the syringe of the present disclosure, the inner chamber 400 is inserted into the above-described insertion portion 320 of the outer chamber 300 according to the embodiment so that the precise branch channels 500 may be formed. In addition, in the syringe of the present disclosure, the branch channels 500 may maintain the stably formed state thereof as the inner chamber 400 is inserted into the insertion portion 320 of the outer chamber 300 and then is insert-injection molded. Therefore, the outer chamber 300 with the branch channels 500 may be coupled to the lower housing 200.

Meanwhile, according to another embodiment of the present disclosure, the outer chamber 300 may have the insertion portion 320 with a cylindrical shape of a faceted-cylindrical shape into which the inner chamber 400 other than the conical shape may be inserted and coupled. According to another embodiment, the inner chamber 400 of the present disclosure may include: the first chamber 420 inserted into the first portion of the insertion portion 320 and having the plurality of first branch grooves 422 on the inner surface thereof, the first branch grooves 422 being formed from the center portion of the upper end in the downward direction; and the second chamber 430 inserted into the second portion of the insertion portion 320 to face the first chamber 420. The branch channels 500 are formed such that the inner surface of the second chamber 430 seals the outer sides of the first branch grooves 422.

In other words, according to another embodiment of the present disclosure, the outer chamber 300 and the inner chamber 400 form the branch channels 500 by using a plurality of inner chambers 400, not form the branch channels 500 by suing the inner surface of the outer chamber 300. With the above method, as amount of branching is increased, further stable and easy formation of the branch channels 500 may be realized.

Herein, the first chamber 420 and the second chamber 430 of the inner chamber 400 is shaped to be symmetrical each other or to correspond to the insertion portion 320 while being coupled to each other, so that the first chamber 420 and the second chamber 430 are obviously inserted into the insertion portion 320. In the drawings, when two injection nozzles 600 is formed, the two chambers are divided to form the branch channels 500, but when more injection nozzles 600, i.e., more branch channels 500 are formed, more inner chambers 400 may be provided.

Figure 9:
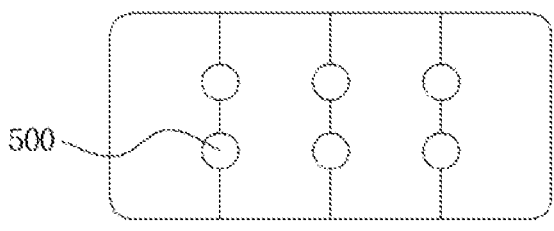
FIG. 9 is a plan view showing an inner chamber of a six-hole type syringe according to another embodiment of the present disclosure.

In addition, when six branch channels 500 are formed and a multi-nozzle with two injection nozzles 600 arranged transversally is formed, as shown in FIG. 9, the inner chamber 400 of the present disclosure may provide the branch channels 500 by using four chambers (not shown).

In addition, when the multi-nozzle with four branch channels 500, i.e. four injection nozzles 600 is formed, according to the embodiment, the inner chamber 400 of the present disclosure is inserted into the conical-shaped insertion portion 320 while having four branch grooves 410, thereby forming the four branch channels 500. Alternately, according to another embodiment, the four the branch channels 500 communicating with the branch portion 310 may be formed by using first, second, and third chambers (not shown).

In addition, according to the another embodiment of the inner chamber 400, the inner chamber 400 is also inserted into and insert-injection molded to the insertion portion 320 of the outer chamber 300, thereby stably maintaining the state in which the branch channels 500 are formed.

Furthermore, the inner chamber 400 of the present disclosure includes: the first chamber 420 inserted into the first portion of the insertion portion 320, and having the first branch grooves 422 on the inner surface, the first branch grooves 422 being formed from the center portion of the upper end of the first chamber 420 in the downward direction; and the second chamber 430 inserted into the second portion of the insertion portion 320 to face the first chamber 420 and having the plurality of second branch grooves 432 formed on an inner surface of the second chamber 430 to face the plurality of first branch grooves 422. The branch channels 500 are formed such that the first branch grooves 422 and the second branch grooves 432 communicated with each other.

In other words, according to another embodiment, the inner chamber 400 is configured to be stacked with all adjacent chambers respectively having branch grooves, not only one chamber having a branch groove, thereby forming the branch channels 500. Therefore, the inner chamber 400 may form more stable and precise cylinder flow path, and thus the inner chamber 400 may efficiently communicate with the injection channels 610 of the injection nozzles 600, which will be described in detail later.

With respect to the above-described configuration, the outer chamber 300 and the inner chamber 400 of the present disclosure are preferably made of a synthetic resin material. The above-described material not only may reduce the manufacturing cost of the syringe, but also realize more precise formation of the branch channels 500.

Herein, like the injection nozzles 600 to be described in detail later, the outer chamber 300 and the inner chamber 400 of the present disclosure may be made of a zirconium-based ceramic material. Specifically, it is preferable that the outer chamber 300 and the inner chamber 400 are made of a zirconium oxide (zirconia) material among zirconium-based ceramic materials. Zirconium oxide has low thermal conductivity thereby preventing the drug from being altered due to thermal transfer when laser is emitted, and has high fracture toughness and high resistance to fracture propagation. Therefore, it is possible to minimize damages or deformation to ends of injection passages, i.e., the branch channels 500 and the injection channels 610 in microjet injection.

As a main component for achieving the present disclosure, the injection nozzles 600 include the injection channels 610, respectively. Each of the injection channels 610 is coupled to the lower portion of the inner chamber 400 and is connected to each of the branch channels 500. The injection nozzles 600 include a plurality of injection nozzles 600 corresponding to a plurality of injection channels 610, thereby delivering the drug solution 20 to a plurality of parts.

Specifically, the injection nozzles 600 of the present disclosure may be integrally provided on the lower portion of the inner chamber 400 or be removably provided thereon. With the injection nozzles 600 removably provided on the lower portion of the inner chamber 400, when the injection channels 610 are broken, dirty, or clogged, only the injection nozzles 600 may be simply replaced without replacing the entire the inner chamber 400 and the outer chamber 300, so the above configuration of the injection nozzles 600 is also advantageous in terms of maintenance cost.

In addition, each of the injection channels 610 may be shaped in a flared shape in which a portion or the entire portion thereof is gradually expanded with a curved line in an upward direction. The above-described shape may focus pushing the drug solution 20 toward the injection channels 610 by the pressure transmitted from the lower space portion 210, i.e. the branch portion 310. Therefore, the drug solution 20 injected through the injection channels 610 may have greater jet velocity.

Herein, horizontal section areas of the lower space portion 210 of the lower housing 200 and the branch portion 310 of the outer chamber 300 described above are gradually increased in the upward direction within a part or entire section thereof. In each of the lower space portion 210 and the branch portion 310, the inclination of an inner wall of each preset section is constant and the inclination of an inner wall of a plurality of sections may be gradually reduced in the upward direction. The above-described configuration may improve focusing and jet velocity of the drug solution 20 that is injected.

Consequentially, the needleless syringe having a multi-nozzle of the present disclosure is configured to have the branch channels 500 that are formed by the insert method in which the inner chamber 400 is inserted into the outer chamber 300, not a method in which the branch channels 500 are molded at once, in order to form the precise branch channels 500 connected to the precise injection channels 610 formed in the injection nozzles 600 made of a zirconium oxide material. Accordingly, stable and precise injection, i.e. delivery of the drug solution 20 may be performed.

Meanwhile, a manufacturing method for the needleless syringe having a multi-nozzle of the present disclosure will be described as follows.

The manufacturing method for the needleless syringe having a multi-nozzle of the present disclosure is configured by preparing the upper housing 100, the elastic membrane 130, the lower housing 200, and the chamber including the outer chamber 300 and the inner chamber 400 and coupled, at a lower portion thereof, to the injection nozzles 600. The lower housing 200 is coupled to the lower portion of the upper housing 100 with the elastic membrane 130 located between the upper housing 100 and the lower housing 200. The chamber is coupled to the lower portion of the lower housing 200.

Specifically, the manufacturing method includes: preparing at S10, wherein the upper housing 100 with the upper space portion 110, the elastic membrane 130, the lower housing 200 with the lower space portion 210, and the injector 220 are molded; preparing first insert at S20, wherein the outer chamber 300 with the branch portion 310 and the insertion portion 320 that communicates with the branch portion 310 and is provided on the lower portion of the branch portion 310, the inner chamber 400 having an upper portion inserted into the insertion portion 320, and the injection nozzles 600 inserted into the lower portion of the inner chamber 400 are molded; preparing second insert at S30, wherein the upper portion of the inner chamber 400 is inserted into the insertion portion 320 of the outer chamber 300 at the preparing the first insert at S20 to form the branch channels 500; preparing third insert at S40, wherein the injection nozzles 600 with the injection channels 610 communicating with the branch channels 500 are inserted into the plurality of insert portions (not shown) provided in the lower portion of the inner chamber 400 after the preparing the second insert at S30; preparing fourth insert at S50, wherein a fixed housing (not shown) is coupled to an outer portion of the inner chamber 400 after the preparing the third insert at S40; insert-injection molding at S60, wherein after the preparing the fourth insert at S50, the outer chamber 300, the inner chamber 400, the injection nozzles 600, and the fixed housing are put into a mold (not shown) to injection mold a nozzle part (not shown); first coupling at S70, wherein the upper housing 100 and the lower housing 200 are coupled to each other while the elastic membrane 130 is located between the upper housing 100 and the lower housing 200, and the injector 200 is coupled to the outer portion of the lower housing 200; second coupling at S80, wherein after the first coupling at S70, the pressure-generating liquid 10 is filled in the upper space portion 110 of the upper housing 100 and then the pressure-generating unit 120 is coupled to the upper portion of the upper housing 100; third coupling at S90, wherein after the second coupling at S80, the nozzle part is coupled to the lower portion of the lower housing 200; and finishing at S100, wherein the drug solution 20 is filled from the lower space portion 210 of the lower housing 200 to the injection channels 610 of the injection nozzles 600 by the injector 200.

In addition, according to the embodiment, the insertion portion 320 of the outer chamber 300 that are molded in the preparing the first insert at S20 is shaped in the conical shape that is gradually expanded in the downward direction. The inner chamber 400 of molded in the preparing the first insert at S20 has the upper portion that is shaped to correspond to the insertion portion 320, and has the plurality of branch grooves 410 that are formed from the center portion of the upper end of the inner chamber 400 in the downward direction. The branch channels 500 are formed such that the inner chamber 400 is inserted into the insertion portion 320 and then an inner surface of the insertion portion 320 seals outer sides of the branch grooves 410.

In addition, according to another embodiment, the insertion portion 320 of the outer chamber 300 molded in the preparing the first insert at S20 is shaped in a cylinder. The inner chamber 400 molded in the preparing the first insert at S20 includes the first chamber 420 and the second chamber 430. The first chamber 420 is inserted into the first portion of the insertion portion 320 and has the plurality of first branch grooves 422 on the inner surface thereof, the first branch grooves being formed from the center portion of the upper end thereof in the downward direction. The second chamber 430 is inserted into the second portion of the insertion portion 320 to face the first chamber 420. The branch channels 500 are formed by the inner surface of the second chamber 430 sealing the outer portions of the first branch grooves 422 of the first chamber 420.

In addition, as another embodiment, the inner chamber 400 molded in the preparing the first insert at S20 is inserted into the first portion of the insertion portion 320 of the outer chamber 300 of another embodiment. The inner chamber 400 includes the first chamber 420 and the second chamber 430. The first chamber 420 has the first branch grooves 422 on the inner surface thereof, and the first branch grooves 422 are formed from the center portion of the upper end of the first chamber 420 in the downward direction. The second chamber 430 is inserted into the second portion of the insertion portion 320 to face the first chamber 420 and has the second branch grooves 432 on the inner surface thereof, and the second branch grooves 432 are formed to face the first branch grooves 422. The branch channels 500 are formed such that the first branch grooves 422 and the second branch grooves 432 communicate with each other.

Although preferred embodiments of the present disclosure have been described for illustrative purposes, those skilled in the art will appreciate that various modifications, additions and substitutions are possible, without departing from the scope and spirit of the present disclosure as disclosed in the accompanying claims.

The invention claimed is:

1. A needleless syringe having a multi-nozzle, the needleless syringe comprising:
    an upper housing (100) defining a chamber for containing a pressure-generating liquid (10) and including a pressure-generating unit (120) at an upper portion of the upper housing (100);
    a lower housing (200) configured to contain a drug solution (20) and coupled to a lower portion of the upper housing (100);
    an elastic membrane (130) disposed between the upper housing (100) and the lower housing (200) to separate the pressure-generating liquid (10) from the drug solution (20);
    an outer chamber (300) attached to a lower portion of the lower housing (200) and having an insertion portion (320) in fluid communication with an interior of the lower housing (200), the insertion portion (320) being shaped to gradually expand toward a lower end of the outer chamber (300);
    an inner chamber (400) inserted into the insertion portion (320), the inner chamber (400) having a plurality of branch grooves (410) on an outer surface of the inner chamber (400), the plurality of branch grooves (410) being sealed by an inner surface of the insertion portion (320) to define a plurality of branch channels (500); and
    a plurality of injection nozzles (600) of the multi-nozzle coupled to a lower portion of the inner chamber (400), each injection nozzle (600) of the plurality of injection nozzles having an injection channel (610) fluidly connected to a respective one of the plurality of branch channels (500).

2. The needleless syringe of claim 1, wherein the plurality of injection nozzles (600) is made of a zirconium-based ceramic material.

3. The needleless syringe of claim 2, wherein the inner chamber (400) comprises:
    a first chamber (420) inserted into a first portion of the insertion portion (320), and a plurality of first branch grooves (422) on an inner surface of the first chamber (420), the plurality of first branch grooves (422) being formed from a center portion of an upper end of the first chamber (420) in a downward direction; and
    a second chamber (430) inserted into a second portion of the insertion portion (320) to face the first chamber (420), and having a plurality of second branch grooves (432) formed on an inner surface of the second chamber (430) so as to face the plurality of first branch grooves (422),
    wherein the plurality of branch channels (500) is provided such that the plurality of first branch grooves (422) and the plurality of second branch grooves (432) communicate with each other.

4. The needleless syringe of claim 1, wherein the lower housing (200) comprises an injector (220) provided outside a portion of the lower housing (200) and in fluid communication with the interior of the lower housing (200).

5. The needleless syringe of claim 2, wherein the plurality of branch grooves (410) of the inner chamber (400) is formed beginning from a central region of an upper end of the inner chamber (400) and extends in a downward direction.

6. The needleless syringe of claim 2, wherein the inner chamber (400) comprises:

a first chamber (420) inserted into a first portion of the insertion portion (320), and a plurality of first branch grooves (422) on an inner surface of the first chamber (420), the plurality of first branch grooves (422) being formed from a center portion of an upper end of the first chamber (420) in a downward direction; and a second chamber (430) inserted into a second portion of the insertion portion (320) to face the first chamber (420), wherein the plurality of branch channels (500) is provided such that outer sides of the plurality of first branch grooves (422) are sealed by an inner surface of the second chamber (430).

7. A method for manufacturing the needleless syringe of claim 1, the method comprising:

preparing the upper housing (100), the elastic membrane (130), the lower housing (200), and the chamber which comprises the outer chamber (300) and the inner chamber (400), the chamber having the plurality of injection nozzles (600) coupled to the lower portion of the inner chamber (400);

coupling the lower housing (200) to the lower portion of the upper housing (100) with the elastic membrane (130) positioned between the upper housing (100) and the lower housing (200); and coupling the chamber which comprises the outer chamber (300) and the inner chamber (400) to the lower portion of the lower housing (200).

\* \* \* \* \*